United States Patent [19]

Campbell et al.

[11] Patent Number: 4,539,322
[45] Date of Patent: Sep. 3, 1985

[54] DIHYDROPYRIDINE DERIVATIVES AND THEIR USE IN TREATING HEART CONDITIONS AND HYPERTENSION

[75] Inventors: Simon F. Campbell, Deal; Peter E. Cross, Canterbury; John K. Stubbs, Deal, all of England

[73] Assignee: Pfizer Inc., New York, N.Y.

[21] Appl. No.: 528,507

[22] Filed: Sep. 1, 1983

Related U.S. Application Data

[63] Continuation-in-part of Ser. No. 463,092, Feb. 2, 1983, abandoned.

[30] Foreign Application Priority Data

Sep. 4, 1982 [GB] United Kingdom ............... 8225246
Aug. 26, 1983 [EP] European Pat. Off. ........ 83304954.7

[51] Int. Cl.³ .................... A61K 31/495; C07D 401/12
[52] U.S. Cl. ..................................... 514/253; 514/228; 514/230; 514/231; 514/233; 514/234; 514/236; 514/237; 514/238; 514/252; 544/121; 544/295; 544/363; 544/364; 544/365; 544/399; 548/519
[58] Field of Search ............ 544/364, 363, 295, 365, 544/121; 424/250, 251, 248.5, 248.51, 248.52, 248.54, 248.55

[56] References Cited

U.S. PATENT DOCUMENTS

| | | |
|---|---|---|
| 3,808,210 | 4/1974 | Regnier et al. ............... 544/295 |
| 3,905,970 | 9/1975 | Bossert et al. ............... 544/295 |
| 3,905,983 | 9/1975 | Bossert et al. . |
| 3,943,140 | 3/1976 | Bossert et al. . |
| 3,946,027 | 3/1976 | Bossert et al. . |
| 3,946,028 | 3/1976 | Bossert et al. . |
| 4,177,278 | 12/1979 | Bossert et al. ............... 424/266 |
| 4,188,395 | 2/1980 | Bossert et al. ............... 424/266 |

FOREIGN PATENT DOCUMENTS

| | | |
|---|---|---|
| 0031801 | 7/1981 | European Pat. Off. . |
| 0060674 | 9/1982 | European Pat. Off. . |
| 55-47656 | 4/1980 | Japan . |
| 1552911 | 9/1979 | United Kingdom . |
| 2034693 | 6/1980 | United Kingdom . |
| 1585978 | 3/1981 | United Kingdom . |

*Primary Examiner*—Richard L. Raymond
*Assistant Examiner*—James H. Turnipseed
*Attorney, Agent, or Firm*—Charles J. Knuth; Albert E. Frost; James M. McManus

[57] ABSTRACT

1,4-Dihydropyridine derivatives of the formula:

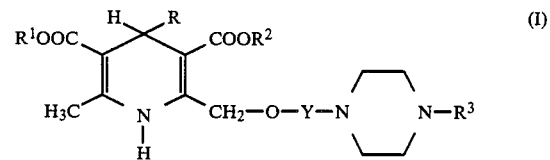

and their pharmaceutically acceptable acid addition salts; where

R is aryl or heteroaryl;
$R^1$ and $R^2$ are each independently $C_1$-$C_4$ alkyl or 2-methoxyethyl;
Y is $-(CH_2)_2-$, $-(CH_2)_3-$, $-CH_2CH(CH_3)-$ or $-CH_2C(CH_3)_2-$;
$R^3$ is hydrogen or an organic substituent are useful in treating or preventing heart conditions or hypertension.

20 Claims, No Drawings

DIHYDROPYRIDINE DERIVATIVES AND THEIR USE IN TREATING HEART CONDITIONS AND HYPERTENSION

This application is a continuation-in-part of Ser. No. 463,092, filed Feb. 2, 1983 now abandoned.

BACKGROUND OF THE INVENTION

This invention relates to certain dihydropyridines, specifically to certain 1,4-dihydropyridines having an optionally substituted piperazinyl group in a side chain attached to the 2-position, which have utility as anti-ischaemic and antihypertensive agents.

The compounds of the invention reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment or prevention of a variety of cardiac conditions, such as angina pectoris, cardiac arrythmias, heart attacks and cardiac hypertrophy. The compounds also have vasodilator activity since they can inhibit calcium influx in cells of vascular tissue and they are thus also useful as antihypertensive agents and for the treatment of coronary vasospasm.

SUMMARY OF THE INVENTION

According to the invention, there are provided novel 1,4-dihydropyridine derivatives of the formula:

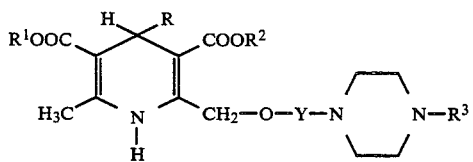

and their pharmaceutically acceptable acid addition salts;
where
R is aryl or heteroaryl;
$R^1$ and $R^2$ are each independently $C_1$-$C_4$ alkyl or 2-methoxyethyl;
Y is —$(CH_2)_2$—, —$(CH_2)_3$—, —$CH_2CH(CH_3)$— or —$CH_2C(CH_3)_2$—;
$R^3$ is hydrogen or a group selected from:
(a)

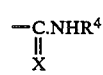

where $R^4$ is H, $C_1$-$C_4$ alkyl, $C_3$-$C_6$ cycloalkyl, —COO($C_1$-$C_4$ alkyl), —$CH_2COO(C_1$-$C_4$ alkyl), aryl, —$SO_2$ aryl, or heteroaryl, and X is O or S;
(b)

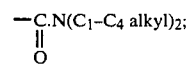

(c)

where $R^5$ is 1-pyrrolidinyl, —$NH_2$, —NH($C_1$-$C_4$ alkyl), —N($C_1$-$C_4$ alkyl)$_2$, or —NH($CH_2)_2$N(-$C_1$-$C_4$ alkyl)$_2$;
(d)

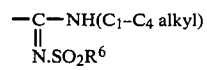

where $R^6$ is $C_1$-$C_4$ alkyl or aryl;
(e)

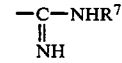

where $R^7$ is —CONH($C_1$-$C_4$ alkyl) or —COO($C_1$-$C_4$ alkyl);
(f)

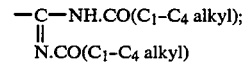

(g)

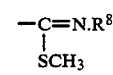

where $R^8$ is —CN, —$SO_2(C_1$-$C_4$ alkyl) or —$SO_2$ aryl;
(h) —$CH_2CO.R^9$ where $R^9$ is —$NH_2$, —NH.($C_1$-$C_4$ alkyl), —NH.aryl or $C_1$-$C_4$ alkoxy;
(i) —$SO_2.R^{10}$ where $R^{10}$ is —$NH_2$, —N($C_1$-$C_4$ alkyl)-$_2$, aryl or $C_1$-$C_4$ alkyl; and
(j) —$CO.R^{11}$ where $R^{11}$ is H, halomethyl, —COO($C_1$-$C_4$ alkyl), —$CH_2O(C_1$-$C_4$ alkyl), —$CH_2CO(C_1$-$C_4$ alkyl), $C_1$-$C_4$ alkyl, $C_1$-$C_4$ alkoxy, aryl, heteroaryl, morpholino or 5-oxo-pyrrolidin-2-yl.

The term "aryl" as used in this specification includes phenyl and phenyl substituted by, for example, one or two substituents selected from nitro, halo, $C_1$-$C_4$ alkyl, $C_1$-$C_4$ alkoxy, hydroxy, trifluoromethyl, ($C_1$-$C_4$ alkoxy)carbonyl and cyano. It also includes 1- and 2-naphthyl.

The term "heteroaryl" as used in this specification means an aromatic heterocyclic group which may optionally be substituted and includes, for example, benzofuranyl; benzothienyl; pyridyl optionally monosubstituted by methyl or cyano; quinolyl; benzoxazolyl; benzthiazolyl; furyl; pyrimidinyl; thiazolyl; 2,1,3-benzoxadiazol-4-yl; 2,1,3-benzthiadiazol-4-yl; and thienyl optionally monosubstituted by halo or $C_1$-$C_4$ alkyl.

"Halo" means fluoro, chloro, bromo or iodo.

Alkyl and alkoxy groups having 3 or more carbon atoms can be straight or branched chain.

R is preferably aryl substituted by 1 or 2 halo atoms or a single $CF_3$ group. The more preferred aryl groups represented by R are 2-chlorophenyl, 2-trifluoromethylphenyl, 2,3-dichlorophenyl, 3,5-dichlorophenyl, 2,6-dichlorophenyl, 1-naphthyl, 3-chlorophenyl and 2-fluorophenyl.

$R^1$ is preferably $CH_3$.

$R^2$ is preferably $C_2H_5$. Y is preferably —$(CH_2)_2$—.

$R^3$ is preferably —$CONH(C_1-C_4\ alkyl)$, most preferably —$CONHCH_3$.

The present invention also includes pharmaceutical compositions containing a compound of the present invention and a pharmaceutically-acceptable diluent or carrier.

Also embraced by this invention are a method for preventing or treating in man either a heart condition or hypertension by administering an effective amount of a compound of the present invention.

DETAILED DESCRIPTION OF THE INVENTION

The compounds of the formula (I) containing one or more asymmetric centres will exist as one or more pairs of enantiomers, and such pairs or individual isomers may be separable by physical methods, e.g. by fractional crystallisation of the free bases or suitable salts or chromatography of the free bases. The invention includes the separated pairs as well as mixtures thereof, as racemic mixtures or as separated d- and l- optically-active isomeric forms.

The pharmaceutically acceptable acid addition salts of the compounds of the formula (I) are those formed from acids which form non-toxic acid addition salts, for example by hydrochloride, hydrobromide, sulphate or bisulphate, phosphate or acid phosphate, acetate, citrate, fumarate, gluconate, lactate, maleate, succinate and tartrate salts.

The compounds of the formula (I) can be prepared by a number of routes, including the following:

(1) Compounds of the formula (I) in which $R^3$ is H can be prepared by the removal of a suitable protecting group from the corresponding N-protected piperazine derivative, i.e.:

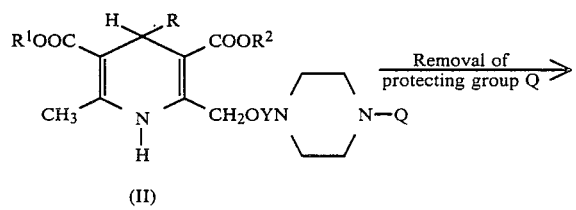

(II)

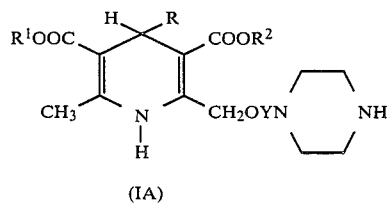

(IA)

Preferred protecting groups are benzyl, 4-chlorobenzyl (both removable by hydrogenation) and trityl (removable by acid).

The N-protected piperazines are obtainable conventionally. The N-benzyl and N-(4-chlorobenzyl) derivatives are for example described and claimed in our European patent application publication no. 0060674 which is incorporated herein by reference.

Routes to these starting materials are as follows:

(a) Hantzsch synthesis:

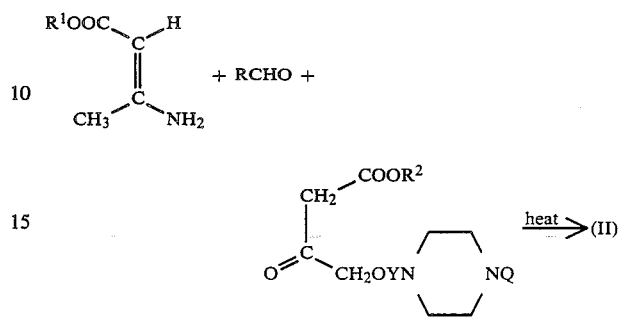

Either the ketoester and aldehyde are heated together first and then the crotonate is added, or all three reactants are heated together, as will be known to those skilled in the art, or (b)

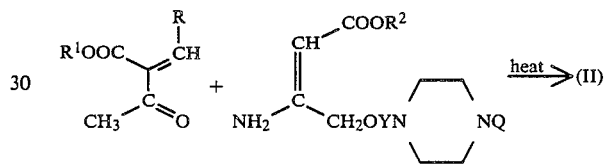

Generally the crotonate is prepared in situ by reaction of the corresponding acetoacetate:

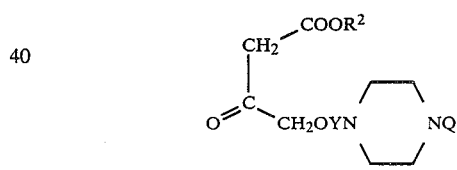

with ammonium acetate as is known to those skilled in the art.

(2) Compounds of the formula (I) in which $R^3$ is $$-\underset{\underset{X}{\|}}{C}NHR^4$$

where $R^4$ is other than H can be prepared by the reaction of a compound of the formula (IA) [see route (1) above] with an isocyanate or isothiocyanate of the formula $R^4.NCX$, i.e.,

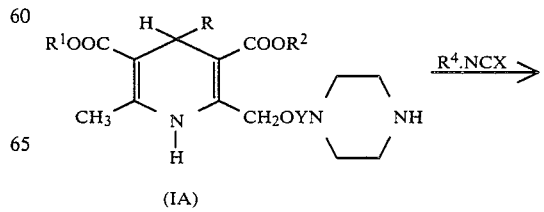

(IA)

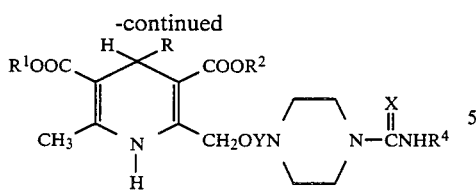

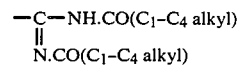

The reaction is carried out conventionally. Generally reaction for a few hours at room temperature in a suitable organic solvent, e.g. methylene chloride, is sufficient.

To prepare compounds in which $R^4$ is H, sodium or potassium cyanate or isothiocyanate in the presence of acid (e.g. acetic acid) should be used. The acid can be supplied by using (IA) as an acid addition salt.

(3) Many of the compounds of the formula (I) can be prepared by the alkylation or acylation of compound (IA):

—C—NH.CO($C_1$-$C_4$ alkyl)
∥
N.CO($C_1$-$C_4$ alkyl)

can be prepared as follows:

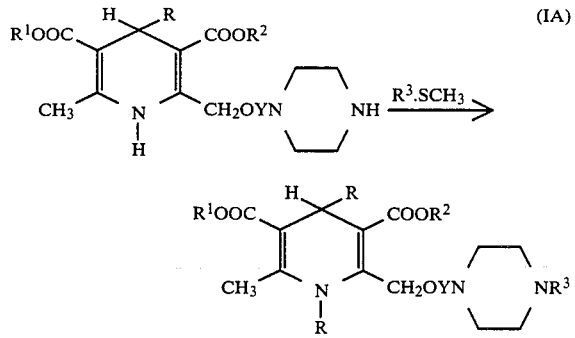

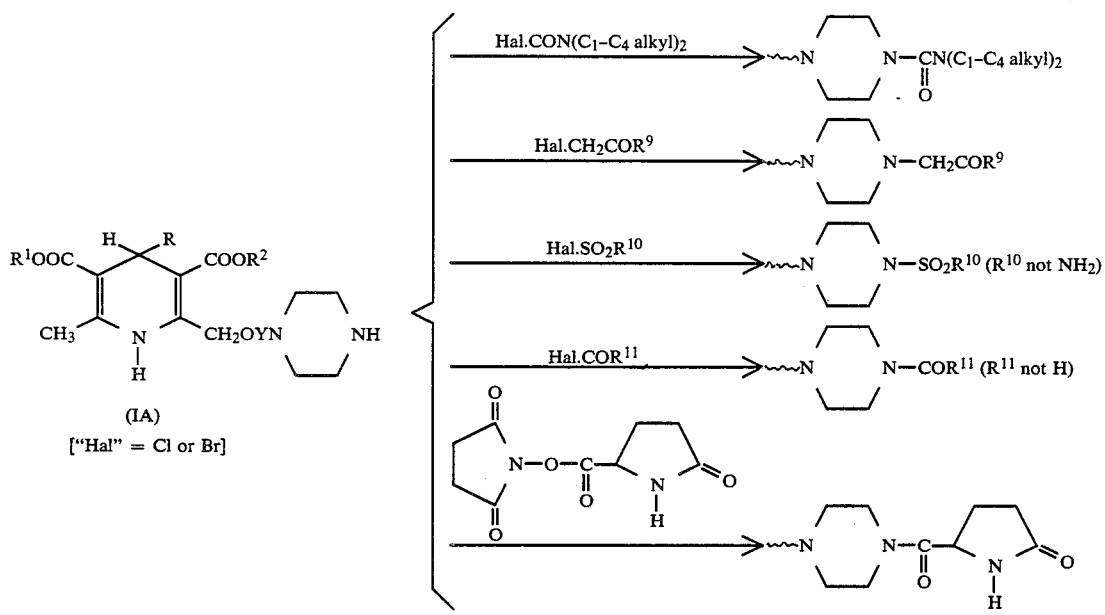

These reactions are carried out conventionally. When using a halide or acid halide reactant, the presence of an acid acceptor such as sodium carbonate or diethylamine is desirable. In many cases the reaction will proceed to completion by stirring the reactants together at room temperature in a suitable organic solvent, e.g. methylene chloride. In some cases heating, e.g. at reflux, is desirable to ensure that the reaction proceeds to completion in a reasonable period.

(4) The compounds of the formula (I) in which $R^3$ is

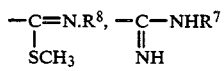

or

The reaction is typically carried out by heating the reactants, preferably under reflux, in a suitable organic solvent, e.g. isopropanol, for up to, say, 6 hours.

(5) The compounds of the formula (I) in which $R^3$ is

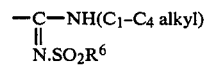

can be prepared as follows:

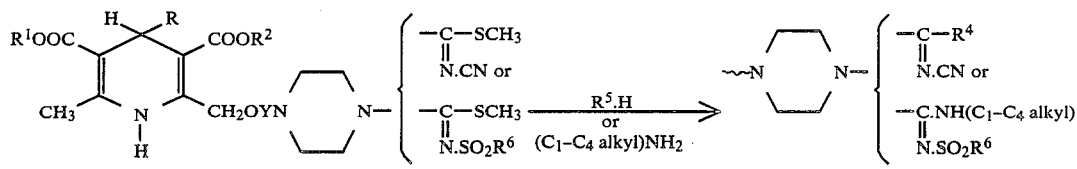

The reaction is typically carried out by heating the reactants, e.g. under reflux, in a suitable organic solvent, e.g. ethanol, for a few hours.

(6) The compounds of the formula (I) in which $R^{10}$ is —$NH_2$ (i.e. $R^3$=—$SO_2NH_2$) can be prepared as follows:

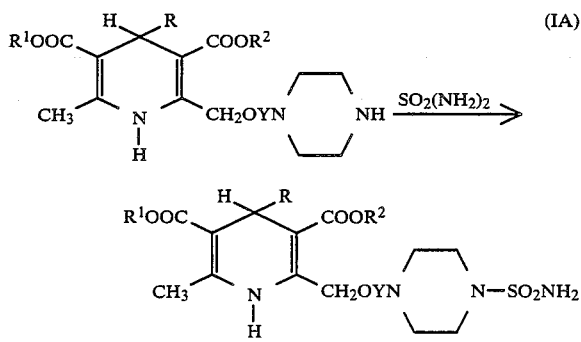

The reaction is typically carried out by heating the reactants together for a few hours, preferably under reflux, in a suitable organic solvent, e.g. dioxan.

(7) The compounds of the formula (I) in which $R^3$ is —$COCH_2COCH_3$ can be prepared as follows:

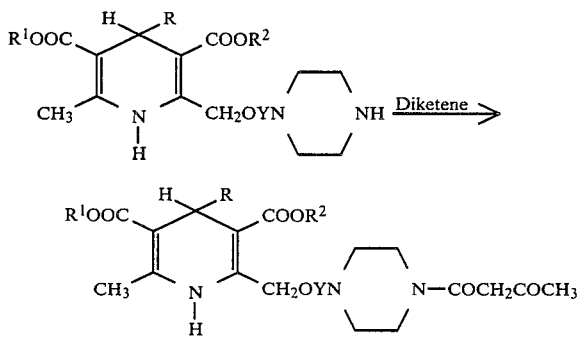

The reaction is typically carried out by stirring the reactants at room temperature in a suitable organic solvent, e.g. acetonitrile, for a short period.

(8) The compounds of the formula (I) in which $R^{11}$ is H (i.e. $R^3$ is —CHO) can be prepared as follows:

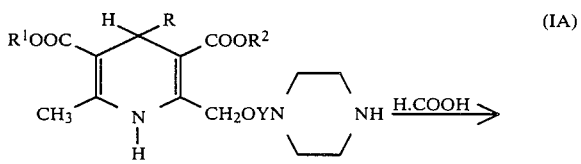

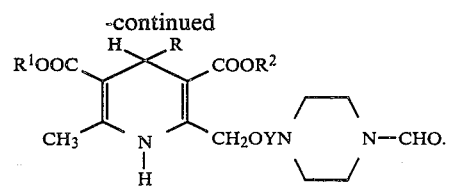

The reaction is typically carried out by heating the piperazine (IA) in 98% formic acid for a short period.

and (9) Acid addition salts can be prepared conventionally, e.g. by reacting a solution of the free base in a suitable organic solvent with a solution of the desired acid in a suitable solvent, and either recovering the salt by filtration where it precipitates from solution, or by evaporation of solution to dryness.

The ability of the compounds to inhibit the movement of calcium into the cell is shown by their effectiveness in reducing the response of isolated heart tissue to an increase in calcium ion concentration in vitro. The test is performed by mounting spirally cut strips of rat aorta with one end fixed and the other attached to a force transducer. The tissue is immersed in a bath of physiological saline solution containing potassium ion s at a concentration of 45 millimolar and no calcium. Calcium chloride is added to the bath with a pipette to give a final calcium ion concentration of 2 millimolar. The change in tension caused by the resulting contraction of the tissue is noted. The bath is drained and replaced with fresh saline solution and, after 45 minutes, the test is repeated with the particular compound under test present in the saline solution. The concentration of compound required to reduce the response by 50% is recorded.

The antihypertensive activity of the compounds is also evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds are generally in the range of from 2-100 mg daily for an average adult patient (70 kg). Thus for a typical adult patient, individual tablets or capsules generally contain from 1 to 10 mg of active compound, in a suitable pharmaceutically acceptable vehicle or carrier. Dosages for intravenous administration are typically within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosages ranges are merited, and such are within the scope of this invention.

For human use, the compounds of the formula (I) can be administered alone, but are generally administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

Thus in a further aspect the invention provides a pharmaceutical composition comprising a compound of the formula (I), or a pharmaceutically acceptable acid addition salt thereof, together with a pharmaceutically acceptable diluent or carrier.

The invention also provides a method of protecting the heart from the deleterious effects of ischaemia, which comprises administering an effective amount of a compound of the formula (I) or pharmaceutically acceptable acid addition salt thereof, or pharmaceutical composition as defined above.

The invention also includes a method of treating hypertension which comprises administering an antihypertensive amount of a compound of the formula (I) or pharmaceutically acceptable acid addition salt thereof, or pharmaceutical composition as defined above.

The following Examples illustrate the invention:

EXAMPLE 1

Preparation of 4-(2-chlorophenyl)-2-[2-[4-(N-cyano-N'-methylamidino)piperazin-1-yl]ethoxymethyl]-3-ethoxycarbonyl-5-methoxy-carbonyl-6-methyl-1,4-dihydropyridine, oxalate salt

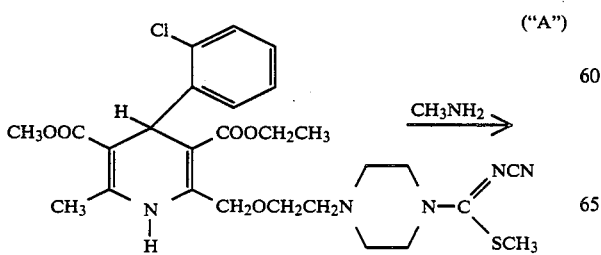

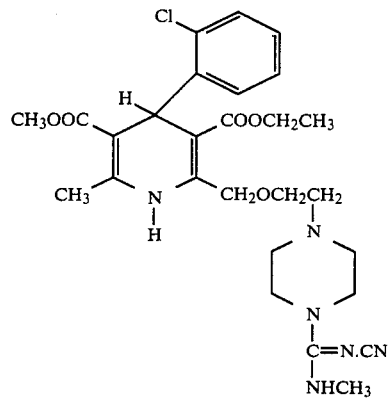

4-(2-Chlorophenyl)-2-[2-[4-(2-cyano-1-methylthioformimidoyl)piperazin-1-yl]-ethoxymethyl]-3-ethoxycarbonyl-5-methoxycarbonyl-6-methyl-1,4-dihydropyridine (Compound "A", see Example 63) (1.5 g) was dissolved in a 33% solution of methylamine in ethanol (20 ml), stood for one hour at room temperature, and then heated under reflux for two hours. The solvent was removed by evaporation, and the residue in a little toluene was chromatographed on a column of "Florisil" (Trade Mark) (6 g), eluting with toluene. Appropriate fractions were combined, evaporated to dryness, and the residue was dissolved in ethyl acetate and then treated with a solution of oxalic acid in ethyl acetate to give the title compound (650 mg), m.p. 165° (decomposes) (from a little methanol).

Analysis %: Calculated for $C_{27}H_{35}ClN_6O_5 \cdot C_2H_2O_4$: C,53.66; H,5.75; N,12.95 Found: C,53.35; H,6.04; N,13.05.

EXAMPLES 2-8

The following compounds were prepared similarly to the previous Example, starting from intermediate "A" and the appropriate amine or ammonia (Examples 2 to 6), or from methylamine and a piperazine starting material having, respectively, $-SO_2CH_3$ or $-SO_2$.phenyl in place of the $-CN$ group of intermediate "A" (Examples 7 and 8), and were characterised in the form indicated.

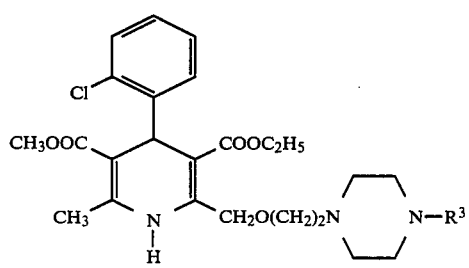

| Example No. | R³ | Form Isolated | m.p. (°C.) | Analysis % (Theoretical in brackets) C | H | N |
|---|---|---|---|---|---|---|
| 2 | NCN / pyrrolidine | Hydrochloride | 146° | 56.51 (56.69 | 6.47 6.34 | 13.08 13.22) |
| 3 | NCN / NHCH(CH₃)₂ | Dihydrochloride | 140° | 52.23 (52.77 | 6.47 6.26 | 12.64 12.73) |
| 4 | NCN / N(CH₃)₂ | Sesquimaleate | 70° | 54.07 (54.65 | 5.76 5.80 | 11.04 11.25) |
| 5 | NCN / NH₂ | Free base | 171–3° | 57.65 (57.30 | 6.31 6.10 | 15.51 15.42) |
| 6 | NCN / NH(CH₂)₂N(CH₃)₂ | Trismaleate | 50° | 51.94 (52.36 | 6.06 5.64 | 9.99 10.17) |
| 7 | NSO₂CH₃ / NHCH₃ | Free base | 90–1° | 52.79 (52.97 | 6.27 6.26 | 10.98 11.44) |
| 8 | NSO₂Ph / NHCH₃ | Maleate, hemihydrate | — (hygroscopic) | 54.06 (54.09 | 5.45 5.68 | 8.71 8.76) |

EXAMPLE 9

The following compound, m.p. 78°–80°, was prepared similarly to Example 1, starting from the corresponding 4-(2,3-dichlorophenyl)-1,4-dihydropyridine and methylamine:

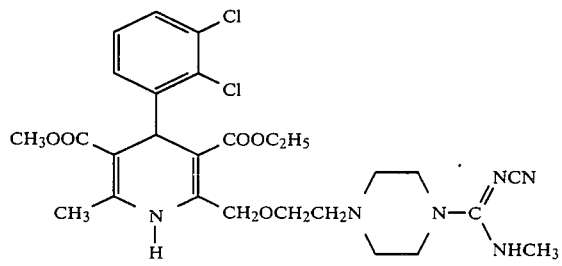

Analysis %: Found: C,53.98; H,5.85; N,13.65; Calculated for $C_{27}H_{34}Cl_2N_6O_5 \cdot \tfrac{1}{2}H_2O$: C,53.82; H,5.86; N,13.95.

EXAMPLE 10

Preparation of 4-(2-chlorophenyl)-3-ethoxycarbonyl-5-methoxy-carbonyl-6-methyl-2-[2-(4-(N-methylthiocarbamoyl)-piperazin-1-yl)ethoxymethyl]-1,4-dihydropyridine, hydrochloride salt

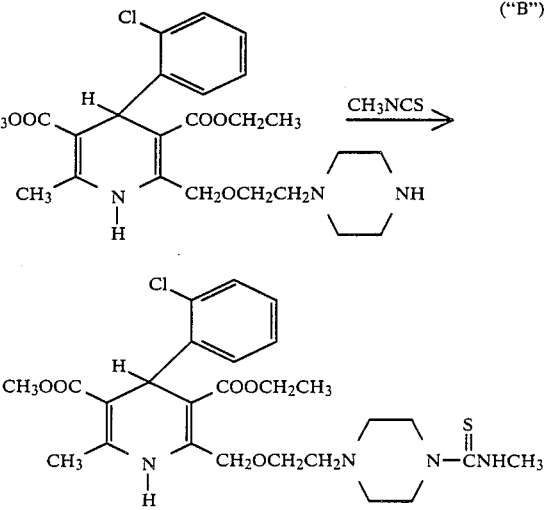

The piperazine "B" (see Example 55) (0.5 g) was dissolved in dry methylene chloride (15 ml) and methylisothiocyanate (0.2 g) was added with stirring. After one hour at room temperature the solvent was removed by evaporation. The residue in ethyl acetate was acidified with ethereal hydrogen chloride and again evaporated to dryness. The residue solidified on trituration with dry ether to give the title compound (450 mg), m.p. 168°–170°.

Analysis %: Calculated for $C_{26}H_{35}ClN_4O_5S \cdot HCl$: C,53.15; H,6.18; N,9.54 Found: C,52.96; H,6.22; N,9.65.

EXAMPLES 11-37

The following compounds were prepared similarly to the previous Example, starting from the appropriate piperazine and isocyanate or isothiocyanate, and were characterised in the form indicated. In Example 14, potassium cyanate was used and the piperazine starting material was in the oxalate salt form. In Example 37, potassium cyanate and aqueous acetic acid was used.

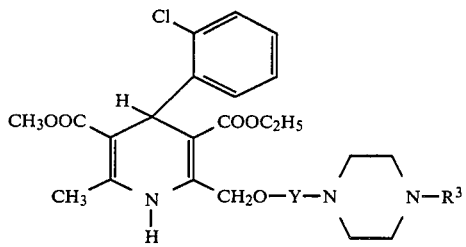

| Example No. | Y | $R^3$ | Form Isolated | m.p. (°C.) | Analysis % (Theoretical in brackets) | | |
|---|---|---|---|---|---|---|---|
| | | | | | C | H | N |
| 11 | $(CH_2)_2$ | $-CSNHCO_2C_2H_5$ | Hydrochloride | 110° | 52.51 (52.09 | 6.05 5.73 | 8.72 8.68) |
| 12 | $(CH_2)_2$ | $-CONHC(CH_3)_3$ | Hydrochloride hemihydrate | 138–140° | 55.84 (55.94 | 6.86 6.96 | 9.19 9.00) |
| 13 | $(CH_2)_2$ | $-CONHCH_3$ | Hydrochloride | 165–7° | 54.49 (54.64 | 6.31 6.35 | 9.67 9.80) |
| 14 | $(CH_2)_2$ | $-CONH_2$ | Dihydrochloride | 150° decomp. | 50.74 (50.55 | 6.02 6.11 | 9.22 9.43) |
| 15 | $(CH_2)_2$ | $-CONHPh$ | Hydrochloride | 130° | 58.48 (58.77 | 5.98 6.05 | 8.54 8.84) |
| 16 | $(CH_2)_2$ | $-CONHSO_2-\text{C}_6H_4-CH_3$ | Hydrate | 200–2° | 55.30 (55.43 | 5.72 5.96 | 8.05 8.08) |
| 17 | $(CH_2)_2$ | $-CONHCH_2CO_2C_2H_5$ | Hydrochloride hemihydrate | 135° | 53.44 (53.37 | 6.28 6.33 | 8.56 8.59) |
| 18 | $(CH_2)_2$ | $-CONH-\text{cyclopropyl}$ | Hydrochloride hydrate | 198–200° | 54.76 (54.63 | 6.28 6.55 | 9.10 9.10) |
| 19 | $(CH_2)_2$ | $-CONH-(CH_2)_3CH_3$ | Hydrochloride | 125° | 56.45 (56.77 | 6.76 6.90 | 8.93 9.13) |
| 20 | $(CH_2)_2$ | $-CONH-\text{C}_6H_4-CO_2C_2H_5$ | Hydrochloride | 216° | 57.70 (57.87 | 6.11 6.00 | 8.29 7.94) |
| 21 | $(CH_2)_2$ | $-CONH-\text{C}_6H_4-F$ | Hydrochloride | 120° | 56.51 (57.14 | 5.59 5.72 | 8.47 8.60) |
| 22 | $(CH_2)_2$ | $-CONHCH(CH_3)_2$ | Free base | 155–6° | 59.80 (59.72 | 7.08 6.98 | 9.82 9.95) |
| 23 | $(CH_2)_2$ | $-CONH-\text{cyclohexyl}$ | Hydrochloride | 155° | 58.07 (58.21 | 6.87 6.83 | 8.98 8.76) |
| 24 | $(CH_2)_2$ | $-CONH-\text{pyridyl}$ | Trihydrochloride | 90° | 50.52 (50.92 | 5.70 5.56 | 9.66 9.90) |
| 25 | $(CH_2)_2$ | $-CONH(CH_2)_2CH_3$ | Hydrochloride | 105° | 54.09 (54.45 | 6.61 6.86 | 8.73 9.07) |
| 26 | $-CH_2CH(CH_3)-$ | $-CONHCH_3$ | Hydrochloride | 185° | 55.20 (55.38 | 6.43 6.54 | 9.67 9.57) |
| 27 | $-CH_2CH(CH_3)-$ | $-CONHC_2H_5$ | Hydrochloride | 140° | 55.34 (56.09 | 6.67 6.72 | 9.12 9.35) |

| | | | | | | | |
|---|---|---|---|---|---|---|---|
| 28 | —CH₂CH(CH₃)— | —CONHCH(CH₃)₂— | Hydrochloride | 115° | 56.29 (56.77 | 6.90 6.90 | 9.11 9.13) |
| 29 | —CH₂C(CH₃)₂ | —CONHCH₃ | Hydrochloride | 180–3° | 55.64 (56.09 | 6.65 6.72 | 9.03 9.35) |

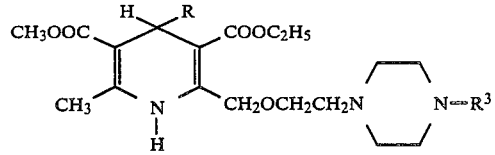

| Example No. | R | R³ | Form Isolated | m.p. (°C.) | Analysis % (Theoretical in brackets) | | |
|---|---|---|---|---|---|---|---|
| | | | | | C | H | N |
| 30 | 2-CF₃—phenyl | —CONHCH₃ | Free Base | 73–75° | 57.17 (57.03 | 6.22 6.20 | 10.07 9.85) |
| 31 | 2,3-dichlorophenyl | —CONHCH₃ | Free Base | 72–74° | 54.18 (54.84 | 5.96 6.02 | 9.93 9.84) |
| 32 | 3,5-dichlorophenyl | —CONHCH₃ | Hemihydrate | 72–74° | 54.10 (53.98 | 6.09 6.10 | 9.71 9.68) |
| 33 | 2,6-dichlorophenyl | —CONHCH₃ | Hemihydrate | 160–162° | 53.58 (53.98 | 5.99 6.10 | 9.65 9.68) |
| 34 | 3-chlorophenyl | —CONHCH₃ | Free Base | 69–71° | 58.41 (58.37 | 6.70 6.59 | 10.46 10.47) |
| 35 | 2-fluorophenyl | —CONHCH₃ | Hydrate | 84–85° | 58.04 (58.19 | 6.78 6.95 | 10.70 10.44) |
| 36 | 2-thiazolyl | —CONHCH₃ | Hemihydrate | 142–143° | 53.25 (53.47 | 6.51 6.63 | 12.97 13.56) |
| 37 | 2,3-dichlorophenyl | —CONH₂ | Hemihydrate | 57° | 53.10 (53.19 | 5.73 5.89 | 9.78 9.93) |

EXAMPLE 38

Preparation of 4-(2-chlorophenyl)-2-[2-[4-(N-[2,6-dimethylphenyl]carbamoylmethyl)piperazin-1-yl]ethoxymethyl]-3-ethoxycarbonyl-5-methoxycarbonyl-6-methyl-1,4-dihydropyridine

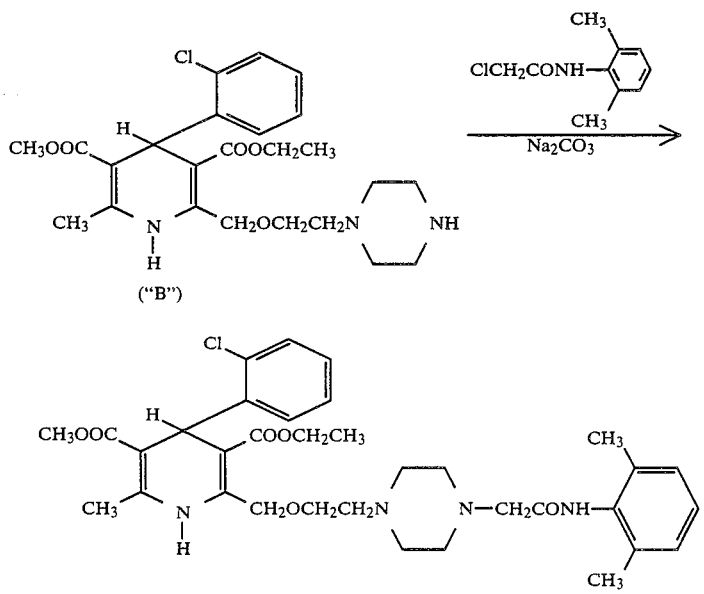

The piperazine "B" (see Example 55) (0.5 g), N-chloroacetyl-2,6-dimethylaniline (0.21 g) and anhydrous sodium carbonate (0.5 g) in dry methylene chloride (10 ml) were stirred and heated under reflux for 3 hours. The solution was then filtered, evaporated to dryness and the residue in toluene/ether (1:1) was chromatographed on "Florisil" (Trade Mark) (3 g) eluting with toluene/ether (1:1), toluene and then chloroform. Appropriate fractions were combined, evaporated to dryness and the residue crystallised from ether to give the title compound (175 mg), m.p. 162°.

Analysis %: Calculated for C₃₄H₄₃ClN₄O₆: C,63.89; H,6.78; N,8.77 Found: C,63.67; H,6.54; N,8.56.

EXAMPLES 39 AND 40

The following compounds were prepared similarly to the method described in the previous Example, starting from compound "B" and either ClCH₂CO₂CH₃ or ClCH₂CONH₂ respectively, and were characterised in the form indicated.

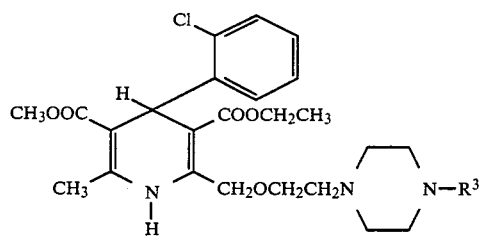

from piperazine "B" and appropriate acyl, sulphonyl or carbamoyl chloride, and were characterised in the form indicated.

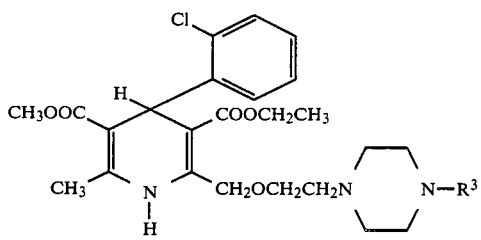

| Example No. | R³ | Solvent | Base | Reaction Time | Form Isolated | m.p. (°C.) | Analysis % (Theoretical in brackets) | | |
|---|---|---|---|---|---|---|---|---|---|
| | | | | | | | C | H | N |
| 39 | —CH₂COOCH₃ | CH₂Cl₂ | Na₂CO₃ | 18 hours | Dihydro-chloride | 110° | 52.06 (52.05 | 6.40 6.15 | 6.72 6.75) |
| 40 | —CH₂CONH₂ | CH₃CH₂OH | N(CH₂CH₃)₃ | 18 hours | Bis-oxalate | 160° | 49.72 (50.39 | 5.49 5.50 | 7.65 7.83) |

EXAMPLE 41

Preparation of 4-(2-chlorophenyl)-2-[2-(4-[N,N-dimethylcarbamoyl]-piperazin-1-yl)ethoxymethyl]-3-ethoxycarbonyl-5-methoxycarbonyl-6-methyl-1,4-dihydropyridine, hydrochloride salt

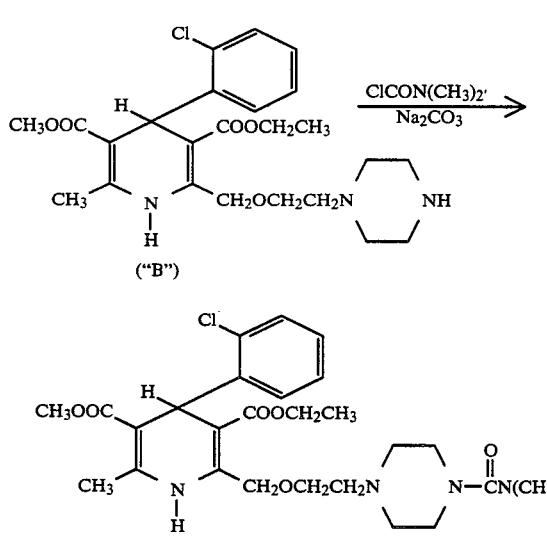

The piperazine "B" (0.5 g) and anhydrous sodium carbonate (0.2 g) were stirred at room temperature in dry methylene chloride (15 ml) and dimethylcarbamoyl chloride (0.1 ml) was added. After one hour, aqueous sodium carbonate (5 ml) was added and the organic layer was separated, dried (Na₂CO₃), filtered and evaporated to dryness. The residue in ethyl acetate was acidified with ethereal hydrogen chloride and again evaporated to dryness. The residue was triturated with dry ether to give the title compound (350 mg), m.p. 202°–204° (from isopropanol).

Analysis %: Calculated for C₂₇H₃₇ClN₄O₆.HCl: C,55.38; H,6.54; N,9.57 Found: C,55.00; H,6.45; N,9.75.

EXAMPLES 42–50

The following compounds were prepared similarly to the method described in the previous Example, starting

| Example No. | R³ | Form Isolated | m.p. (°C.) | Analysis % (Theoretical in brackets) | | |
|---|---|---|---|---|---|---|
| | | | | C | H | N |
| 42 | —SO₂N(CH₃)₂ | Hydro-chloride | 115° | 49.70 (50.24 | 6.09 6.16 | 8.95 9.01) |
| 43 | —SO₂CH₃ | Oxalate | 120° | 49.98 (50.19 | 5.62 5.62 | 6.21 6.50) |
| 44 | —CO-(furyl) | Hydro-chloride | 120° | 56.76 (57.23 | 5.86 5.79 | 6.64 6.90) |
| 45 | —COCO₂CH₂CH₃ | Hydro-chloride | 110° | 54.36 (54.73 | 6.13 6.07 | 6.59 6.84) |
| 46 | —COCH₂OCH₃ | Hydro-chloride | 90° | 54.92 (55.29 | 6.35 6.36 | 7.09 7.16) |
| 47 | —COCH₂Cl | Hydro-chloride | 75° | 52.36 (52.85 | 5.47 5.80 | 6.97 7.11) |
| 48 | —CO-(pyridyl) | Tri-hydro-chloride | 120° | 52.19 (52.03 | 5.59 5.53 | 7.85 8.09) |
| 49 | —CO₂CH₂CH₃ | Hydro-chloride | 130° | 55.32 (55.29 | 6.53 6.36 | 7.00 7.16) |
| 50 | —CON(morpholino) | Free base | 150° | 58.82 (58.93 | 6.61 6.65 | 9.17 9.48) |

EXAMPLE 51

Preparation of
4-(2-chlorophenyl)-3-ethoxycarbonyl-2-[2-(4-formyl-piperazin-1-yl)ethoxymethyl]-5-methoxycarbonyl-6-methyl-1,4-dihydropyridine, bisoxalate salt

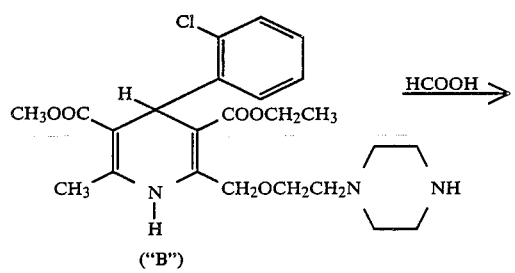

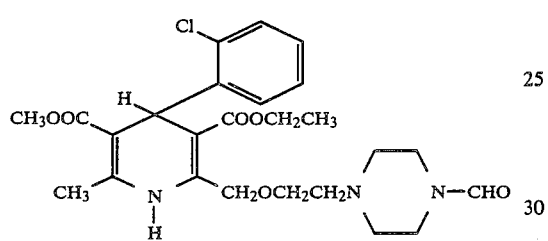

The piperazine "B" (1 g) was dissolved in 98% formic acid (10 ml) and heated on a steam bath for 15 minutes. The solvent was removed by evaporation and the residue was partitioned between ethylacetate (30 ml) and saturated aqueous sodium carbonate (30 ml). The organic phase was dried ($Na_2CO_3$), filtered, and treated with a solution of oxalic acid in ethyl acetate to give the title compound, (95 mg.), m.p. 85°.

Analysis %: Calculated for $C_{25}H_{32}ClN_3O_6.2(C_2H_2O_4)$: C,50.92; H,5.01; N,6.14 Found: C,50.48; H,5.47; N,5.96.

EXAMPLE 52

Preparation of
2-[2-(4-acetoacetylpiperazin-1-yl)ethoxymethyl]-4-(2-chlorophenyl)-3-ethoxycarbonyl-5-methoxycarbonyl-6-methyl-1,4-dihydropyridine, hydrochloride hydrate

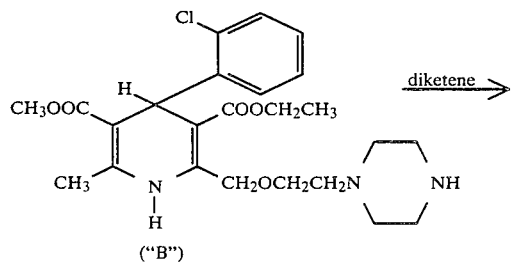

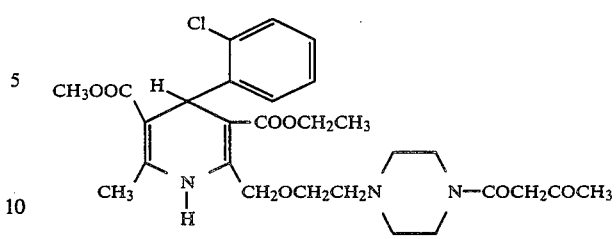

The piperazine "B" (0.5 g) was dissolved in dry acetonitrile (15 ml) and diketene (0.2 ml) was added. The mixture was stirred at room temperature for 30 minutes and then evaporated to dryness. The residue was dissolved in ethyl acetate and acidified with ethereal hydrogen chloride. The solution was again evaporated to dryness and the residue triturated with dry ether to give the title compound (230 mg), m.p. 95° (foams).

Analysis %: Calculated for $C_{28}H_{36}ClN_3O_7$; HCl; $H_2O$: C,54.54; H,6.38; N,6.81 Found: C,54.97; H,6.22; N,6.64.

EXAMPLE 53

Preparation of
4-(2-chlorophenyl)-3-ethoxycarbonyl-5-methoxycarbonyl-6-methyl-2-[2-(4-sulphamoylpiperazin-1-yl)ethoxymethyl]-1,4-dihydropyridine, hydrochloride hydrate

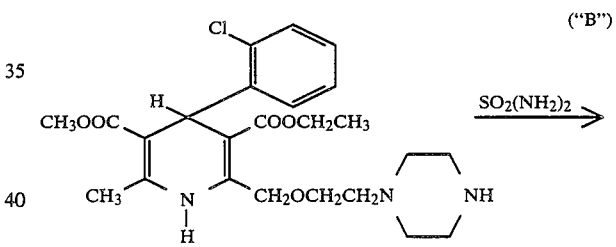

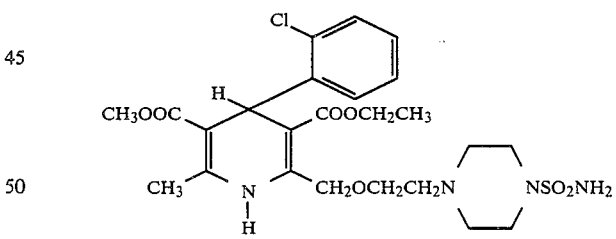

The piperazine "B" (0.5 g) and sulphamide (1.5 g) in dry dioxan (15 ml) were heated under reflux for 1 hour, then evaporated to dryness. The residue was partitioned between methylene chloride (25 ml) and aqueous sodium carbonate (20 ml). The organic phase was dried ($Na_2CO_3$), filtered and evaporated to dryness. The residue was dissolved in ethylacetate and acidified with ethereal hydrogen chloride, then again evaporated to dryness. The residue crystallised from a little ethyl acetate, to give the title compound (180 mg), m.p. 175°–7°.

Analysis %: Calculated for $C_{24}H_{33}ClN_4O_7S$; HCl; $H_2O$: C,47.13; H,5.93; N,9.16 Found: C,46.74; H,5.51; N,9.06.

EXAMPLE 54

Preparation of 4-(2-chlorophenyl)-3-ethoxycarbonyl-5-methoxycarbonyl-6-methyl-2-[2-(4-[1-5-oxo-pyrrolidin-2-ylcarbonyl]-piperazin-1-yl)ethoxymethyl]-1,4-dihydropyridine, hydrochloride hydrate

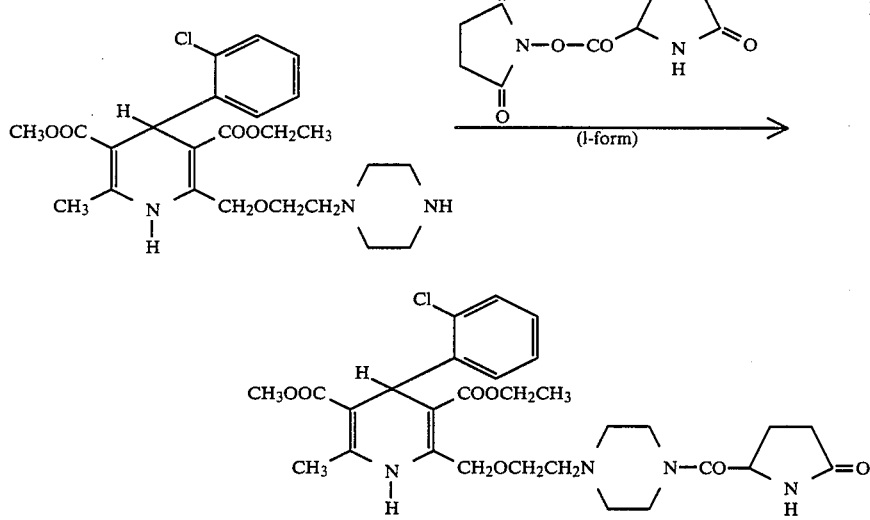

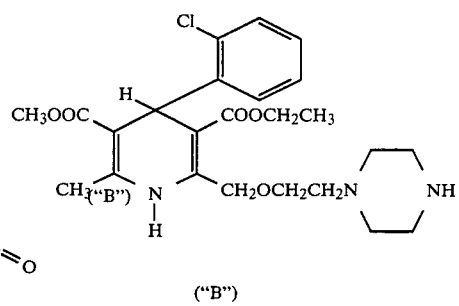

The piperazine "B" (0.5 g) was dissolved in dry THF (15 ml) and 1-5-oxopyrrolidine-2-carboxylic acid, succinimido ester (0.3 g) was added. the reaction mixture was stirred overnight at room temperature and then evaporated to dryness. The residue was partitioned between ethyl acetate (20 ml) and water (20 ml), the organic phase dried (MgSO$_4$) and filtered. The solution was acidified with ethereal hydrogen chloride and evaporated to dryness. Trituration of the residue with dry ether gave the title compound (135 mg), m.p. 150° (foams).

Analysis %: Calculated for C$_{29}$H$_{37}$ClN$_4$O$_7$; HCl; H$_2$O: C,54.12; H,6.26; N,8.70 Found: C,54.09; H,5.96; N,8.64.

EXAMPLE 55

Preparation of 4-(2-chlorophenyl)-3-ethoxycarbonyl-5-methoxycarbonyl-6-methyl-2-[2-(piperazin-1-yl)ethoxymethyl]-1,4-dihydropyridine, and its bis-oxalate salt

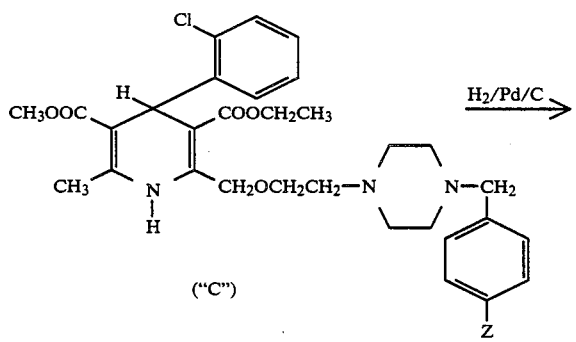

Method A

The bis-oxalate salt of the 4-chlorobenzyl-protected piperazine "C" (Z=Cl) (5 g) in methanol (1500 ml) was stirred and hydrogenated on a 5% palladium on charcoal catalyst (0.5 g) at 50 p.s.i. and room temperature overnight. The catalyst was filtered, the solvent removed by evaporation, and the residue partitioned between methylene chloride (100 ml) and dilute aqueous ammonia (100 ml). The organic phase was dried (Na$_2$CO$_3$), filtered and evaporated to dryness to give the title compound as the free base, an oil (3 g). A sample converted to the bis-oxalate salt in acetone had a m.p. 170° (decomposes).

Analysis %: Calculated for C$_{24}$H$_{32}$ClN$_3$O$_5$.2(C$_2$H$_2$O$_4$): C,51.03; H,5.66; N,6.38 Found: C,51.72; H,5.58; N,6.54.

Method B

The benzyl-protected piperazine "C" (Z=H) (42 g) in methanol (1500 ml) and acetic acid (9 ml) was hydrogenated at 40° under 50 p.s.i. on a 55 palladium on charcoal catalyst (2 g) overnight. Treatment as in Method "A" gave the title compound as the bis-oxalate salt (19 g), identical to the salt obtained by Method "A".

The starting 4-chloro-benzyl- and benzyl-piperazines are described in Examples 34 and 38 respectively of our copending European Patent Application Publication No. 0060674, which is incorporated herein by reference. The route used to them was as follows:

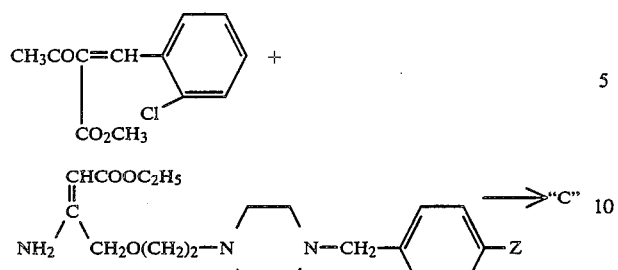

EXAMPLES 56–62

| Example No. | Method | R | Y | Form Isolated | m.p. (°C.) | Analysis % (Theoretical in brackets) C / H / N |
|---|---|---|---|---|---|---|
| 56 | "A" | 2-Cl-phenyl | —CH₂C(CH₃)₂— | Bisoxalate | 120° | 52.53  5.77  5.77 (52.51  5.88  6.12) |
| 57 | "B" | 2-Cl-phenyl | —CH₂CH(CH₃)— | Mono-oxalate | 225–7° | 55.29  6.26  7.14 (55.71  6.23  7.22) |
| 58 | "B" | 2-CF₃-phenyl | —(CH₂)₂— | Free base | N.m.r. (CDCl₃) δ = 1.21 (t) 3H, 2.01 (m) 4H, 2.35 (s) 3H, 2.75 (m) 4H, 3.13 (m) 2H, 3.58 (s) 3H, 3.60 (t) 2H, 3.70 (q) 2H, 4.71 (s) 2H, 5.57 (s) 1H, 6.40 (m) 2H, 7.34 (m) 4H. | |
| 59 | "B" | 2,3-diCl-phenyl | —(CH₂)₂— | Free base | 1.18 (t) 3H, 2.35 (s) 3H, 2.65 (m) 11H, 3.58 (s) 3H, 3.60 (t) 2H, 4.01 (q) 2H, 4.68 (s) 2H, 5.25 (s) 1H, 7.14 (m) 4H, | |
| 60 | "B" | 3,5-diCl-phenyl | —(CH₂)₂— | Free base | 1.18 (t) 3H, 2.38 (s) 3H, 2.85 (m) 11H, 3.60 (s) 3H, 3.60 (broad) 2H, 4.10 (q) 2H, 4.65 (s) 2H, 4.90 (s) 1H, 7.25 (m) 3H, 8.87 (s) 1H. Also I.R. (Nujol) NH 3380 cm⁻¹, C=O 1685 cm⁻¹ | |
| 61 | "B" | 2,6-diCl-phenyl | —(CH₂)₂— | Free base | 1.06 (t) 3H, 2.24 (s) 3H, 2.58 (m) 10H, 3.38 (t) 2H, 3.52 (s) 3H, 3.61 (m) 1H, 3.96 (q) 2H, 4.64 (s) 2H, 5.93 (s) 1H, 7.12 (m) 3H, 7.46 (m) 1H | |
| 62 | "B" | 3-Cl-phenyl | —(CH₂)₂— | Free base | 1.21 (t) 3H, 2.38 (s) 3H, 2.60 (m) 11H, 3.60 (s) 3H, 3.60 (t) 2H, 4.05 (q) 2H, 4.68 (s) 2H, 4.95 (s) 1H, 7.16 (m) 5H Also I.R. (Nujol) NH 3300 cm⁻¹ C=O 1685 cm⁻¹ | |

The following compounds were obtained similarly to the stated method described in the previous Example from appropriate starting materials, and were characterised as stated.

The starting benzyl-protected piperazines used in the hydrogenations of Examples 56 and 57 were prepared similarly to the method described at the end of Example 55.

The starting benzyl-protected piperazines used in the hydrogenations of Examples 58–62 were prepared by the Hantzsch reaction:

(i)

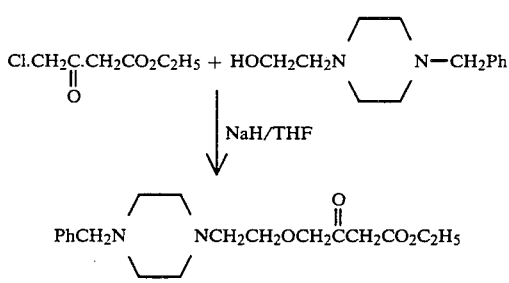

(ii) Hantzsch reaction (see e.g. European Patent Application publication no. 0060674)

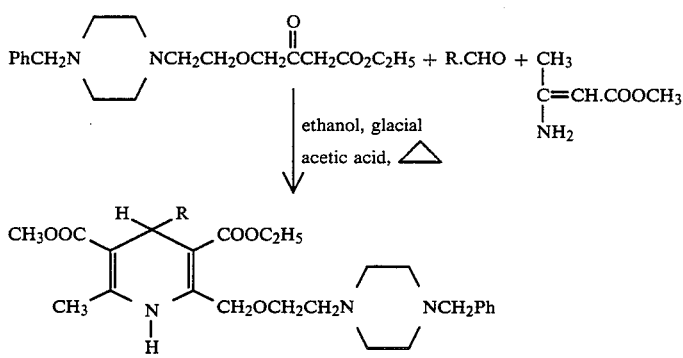

EXAMPLE 63

Preparation of 4-(2-chlorophenyl)-2-[2-[4-(2-cyano-1-methylthioformimidoyl)piperazin-1-yl]ethoxymethyl]-3-ethoxycarbonyl-5-methoxycarbonyl-6-methyl-1,4-dihydropyridine, hydrochloride salt

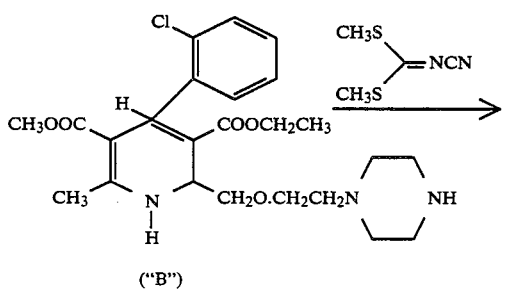

("B")

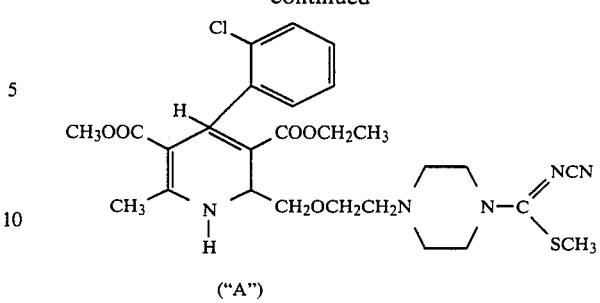

("A")

4-(2-Chlorophenyl)-3-ethoxycarbonyl-5-methoxycarbonyl-6-methyl-2-[2-(piperazin-1-yl)ethoxymethyl]-1,4-dihydropyridine (3.2 g) and dimethyl N-cyanoimidodithiocarbonate (1 g) in isopropanol (100 ml) were heated under reflux for 4 hours. The solvent was then removed by evaporation, and the residue in a little toluene was filtered through "Florisil" (Trade Mark) (5 g) eluting with toluene. Appropriate fractions were combined, evaporated to dryness and the residue was dissolved in ethyl acetate and acidified with ethereal hydrogen chloride. The solvent was removed by evaporation and the residue triturated with dry ether to give the title compound (3 g), m.p. 168°.

Analysis %: Calculated for $C_{27}H_{28}ClN_5O_5S \cdot HCl$: C,52.94; H,5,76; N,11.43 Found: C,52.92; H,5.84; N,11.71.

EXAMPLES 64–69

The following compounds were prepared similarly to the method described in the previous Example, and were characterised in the form indicated.

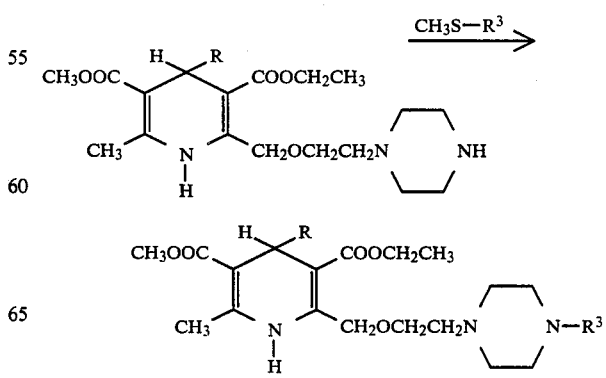

| Example No. | R | R³ | Form Isolated | m.p. (°C.) | C | H | N |
|---|---|---|---|---|---|---|---|
| 64 |  | NH, NHCONHCH(CH₃)₂ | Bis-maleate | 118–120° | 52.89 (53.08 | 5.90 5.90 | 10.09 10.04) |
| 65 |  | NH, NHCOOCH₃ | Bis-maleate | 118–121° | 51.65 (51.89 | 5.57 5.47 | 8.36 8.64) |
| 66 |  | NCOCH₃, NHCOCH₃ | Free base | 156–8° | 57.34 (57.66 | 6.31 6.34 | 11.50 11.59) |
| 67 |  | NSO₂CH₃, SCH₃ | Not Characterised | | | | |
| 68 |  | NSO₂Ph, SCH₃ | | | | | |
| 69 | 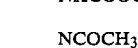 | N.CN, SCH₃ | | | | | |

EXAMPLE 70

(A)

3-Ethoxycarbonyl-5-methoxycarbonyl-6-methyl-4-(1-naphthyl)-2-(2-{piperazin-1-yl}ethoxymethyl)-1,4-dihydropyridine

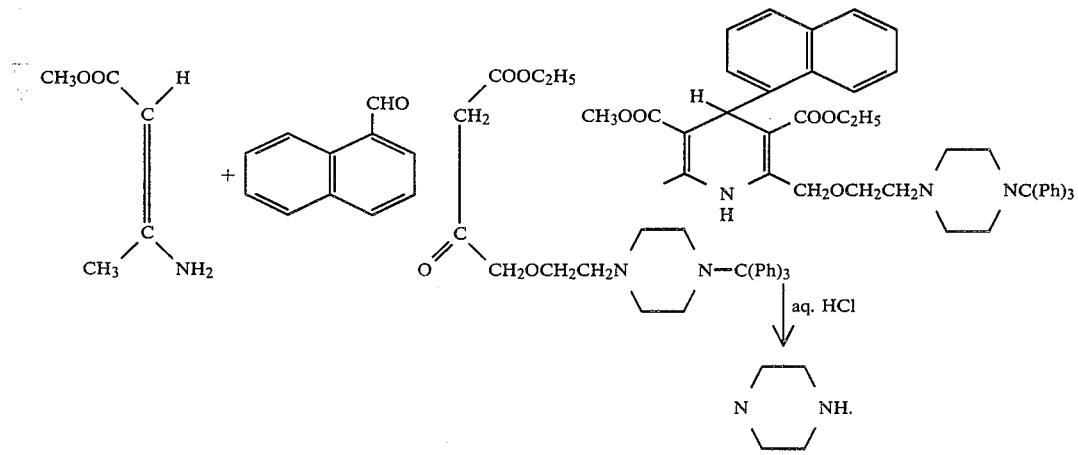

A mixture of 2.6 g of 1-[2-(ethoxycarbonylacetylmethoxy)-ethyl]-1-triphenylmethylpiperazine, 0.81 g 1-naphthaldehyde and 0.6 g of methyl-3-aminocrotonate in 50 ml of methanol was refluxed for 5 hours. After evaporation of the solvent, the residual oily solid was dissolved in diisopropylether, filtered and reevaporated. The resultant oil was stirred in 25 ml of 50% aqueous hydrochloric acid for 1 hour, basified with concentrated aqueous sodium carbonate solution and extracted with methylene chloride to give 1.4 g of 3-ethoxycarbonyl-5-methoxycarbonyl-6-methyl-4-(1-naphthyl)-2-(2-{piperazin-1-yl}ethoxymethyl)-1,4-dihydropyridine as an orange oil, used directly in the next stage.

| N.m.r. (CDCl₃) δ = | 0.92 (t) 3H |
|---|---|
| | 2.42 (s) 3H |
| | 2.73 (m) 10H |
| | 3.41 (s) 3H |
| | 3.75 (q) 2H |
| | 4.10 (t) 2H |
| | 4.76 (s) 2H |
| | 5.80 (s) 1H |
| | 7.50 (m) 7H |
| | 8.55 (m) 1H |

(B)
3-Ethoxycarbonyl-5-methoxycarbonyl-6-methyl-2-{2-[4-(N-methylcarbamoyl)piperazin-1-yl]ethoxymethyl}4-(1-naphthyl)-1,4-dihydropyridine hydrate

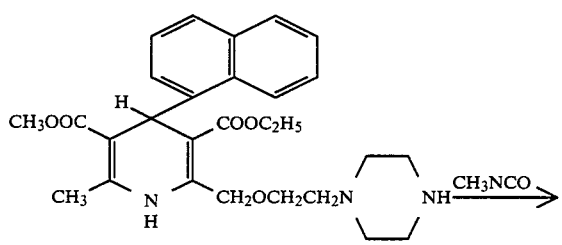

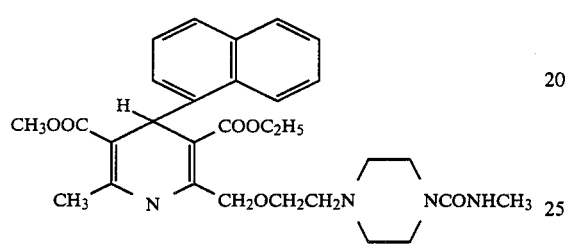

1.3 g of the product of part (A) was dissolved in 5 ml of dry chloroform and a solution of 0.15 g of methylisocyanate in 1 ml of dry chloroform was then added dropwise. The solution was stirred at room temperature for 1 hour and the solvent was then evaporated. The resultant oily solid was chromatographed on 6.0 g "Keiselgel 60" (Trade Mark) using 2% methanol in ethyl acetate to give 0.5 g of a beige solid. This solid was crystallised from ethyl acetate to yield 0.2 g of 3-ethoxycarbonyl-5-methoxycarbonyl-6-methyl-2-{2-[4-(N-methylcarbamoyl)piperazin-1-yl]-ethoxymethyl}-4-(1-naphthyl)-1,4-dihydropyridine hydrate, m.p. 88°.

Analysis %: Found: C,63.39; H,6.82; N,9.87 Required for $C_{30}H_{38}N_4O_6 \cdot H_2O$: C,63.36; H,7.09; N,9.85.

EXAMPLES 71 AND 72

The following compounds were prepared similarly to the previous Example part (A) from appropriate starting materials:

| Example No. | R | Form Isolated | N.M.R. (CDCl₃) δ = |
|---|---|---|---|
| 71 | 2-F-C₆H₄ | Free base | 1.17 (t) 3H, 2.34 (s) 3H, 2.52 (m) 6H, 2.88 (m) 5H, 3.56 (s) 3H, 3.63 (t) 2H, 3.98 (q) 2H, 4.69 (s) 2H, 5.20 (s) 1H, 7.07 (m) 5H, |
| 72 | 2-thiazolyl | Free base | 1.23 (t) 3H, 2.37 (s) 3H, 2.46 (m) 10H, 3.47 (s) 2H, 3.63 (s) 1H, 3.70 (s) 3H, 4.13 (q) 2H, 4.75 (s) 2H, 5.50 (s) 1H, 7.08 (d) 1H, 7.59 (d) 1H, 7.68 (m) 1H |

EXAMPLE 73

Tablets are compounded from the following ingredients:

|  | mg/tablet |
|---|---|
| Product of any one of the Examples | 10 |
| Dicalcium phosphate | 120 |
| Maize starch | 20 |
| Magnesium stearate | 1.8 |
| Sodium lauryl sulphate | 0.2 |

The ingredients are thoroughly blended, compressed, granulated and re-compressed to tablets of the desired size.

EXAMPLE 74

Capsules are compounded from the following ingredients:

|  | mg/capsule |
|---|---|
| Product of any one of the Examples | 10 |
| Maize starch | 127 |
| Cellulose (microcrystalline) | 127 |
| Magnesium stearate | 5.4 |
| Sodium lauryl sulphate | 0.6 |

The ingredients are thoroughly blended, then filled into hard gelatine capsules of the appropriate size to contain the ingredients.

The following Preparation illustrates the preparation of a novel starting material used in Example 70. All temperatures are in °C.:

Preparation 1

(A) 1-(2-Hydroxyethyl)-4-triphenylmethylpiperazine 2.6 g of 1-(2-hydroxyethyl)piperazine was dissolved in a mixture of 20 ml of dry methylene chloride and 10 ml of trimethylamine and stirred at room temperature during the slow addition of a solution of 5.6 g of trityl chloride in 20 ml of dry methylene chloride. When the addition was complete, the solution was stirred for a further 18 hours at room temperature and then evaporated to dryness. Basification with 5% aqueous sodium bicarbonate solution and extraction with methylene chloride gave 4.0 g of 1-(2-hydroxyethyl)-4-triphenylmethylpiperazine, m.p. 82°, used directly in the next stage.

(B)
1-[2-(ethoxycarbonylacetylmethoxy)ethyl]-4-triphenylmethylpiperazine 0.9 g of Sodium hydride was added to 15 ml of dry tetrahydrofuran stirring at room temperature under nitrogen. A solution of 1-(2-hydroxyethyl)-4-triphenylmethylpiperazine in 5 ml of dry tetrahydrofuran was added dropwise and then stirred a further 1 hour after the addition was complete. Finally, a solution of 1.8 g of ethyl 4-chloroacetoacetate in 5 ml of dry tetrahydrofuran was added over 1 hour and the mixture stirred at room temperature for 18 hours. 5 Drops of isopropanol were added to the mixture which was then poured onto 100 g of ice and carefully neutralised with concentrated hydrochloric acid. After extraction with ethyl acetate, the residual oil was dissolved in acetonitrile, washed three times with petroleum ether (40°–60°) and evaporated to give 2.6 g of 1-[2-(ethoxycarbonylacetylmethoxy)ethyl]-4-triphenylmethylpiperazine as an orange-red oil, used directly.

ACTIVITY DATA

The molar concentration of the compounds required to reduce the response by 50% in the test specified on pages 12-13 is given below ($IC_{50}$ values) (1M = 1 gm. mole/liter). The smaller the concentration the more active the compound.

| Compound | $IC_{50}$ |
| --- | --- |
| Product of Example 1 | $1 \times 10^{-8}$ M |
| Product of Example 2 | $1.4 \times 10^{-8}$ M |
| Product of Example 3 | $1 \times 10^{-8}$ M |
| Product of Example 4 | $7 \times 10^{-9}$ M |
| Product of Example 5 | $1 \times 10^{-7}$ M |
| Product of Example 6 | $1 \times 10^{-7}$ M |
| Product of Example 7 | $1 \times 10^{-7}$ M |
| Product of Example 8 | $1.86 \times 10^{-8}$ M |
| Product of Example 9 | $1.51 \times 10^{-8}$ M |
| Product of Example 10 | $6.3 \times 10^{-9}$ M |
| Product of Example 11 | $1.38 \times 10^{-8}$ M |
| Product of Example 12 | $2.0 \times 10^{-9}$ M |
| Product of Example 13 | $6.0 \times 10^{-9}$ M |
| Product of Example 14 | $3.72 \times 10^{-9}$ M |
| Product of Example 15 | $5.01 \times 10^{-9}$ M |
| Product of Example 16 | $2.51 \times 10^{-7}$ M |
| Product of Example 17 | $9.7 \times 10^{-8}$ M |
| Product of Example 18 | $6.92 \times 10^{-9}$ M |
| Product of Example 19 | $1.58 \times 10^{-8}$ M |
| Product of Example 20 | $3.31 \times 10^{-8}$ M |
| Product of Example 21 | $2.19 \times 10^{-8}$ M |
| Product of Example 22 | $2.4 \times 10^{-9}$ M |
| Product of Example 23 | $8.51 \times 10^{-9}$ M |
| Product of Example 24 | $1.45 \times 10^{-8}$ M |
| Product of Example 25 | $7.76 \times 10^{-9}$ M |
| Product of Example 26 | $1.35 \times 10^{-8}$ M |
| Product of Example 27 | $2.1 \times 10^{-8}$ M |
| Product of Example 28 | $9.3 \times 10^{-9}$ M |
| Product of Example 29 | $1.5 \times 10^{-8}$ M |
| Product of Example 30 | $1.1 \times 10^{-8}$ M |
| Product of Example 31 | $2.5 \times 10^{-9}$ M |
| Product of Example 32 | $5 \times 10^{-8}$ M |
| Product of Example 33 | $2.5 \times 10^{-8}$ M |
| Product of Example 34 | $1.78 \times 10^{-8}$ M |
| Product of Example 35 | $1.95 \times 10^{-8}$ M |
| Product of Example 36 | $1 \times 10^{-6}$ M |
| Product of Example 37 | $7.9 \times 10^{-9}$ M |
| Product of Example 38 | $2.04 \times 10^{-8}$ M |
| Product of Example 39 | $1.05 \times 10^{-8}$ M |
| Product of Example 40 | $1.05 \times 10^{-8}$ M |
| Product of Example 41 | $1.29 \times 10^{-8}$ M |
| Product of Example 42 | $4.90 \times 10^{-8}$ M |
| Product of Example 43 | $1.58 \times 10^{-8}$ M |
| Product of Example 44 | $8.51 \times 10^{-8}$ M |
| Product of Example 45 | $1 \times 10^{-8}$ M |
| Product of Example 46 | $6.3 \times 10^{-9}$ M |
| Product of Example 48 | $1.32 \times 10^{-8}$ M |
| Product of Example 49 | $1 \times 10^{-8}$ M |
| Product of Example 50 | $5.9 \times 10^{-9}$ M |
| Product of Example 51 | $7.94 \times 10^{-9}$ M |
| Product of Example 52 | $9.8 \times 10^{-9}$ M |
| Product of Example 53 | $4.17 \times 10^{-8}$ M |
| Product of Example 54 | $3.02 \times 10^{-9}$ M |
| Product of Example 55 | $1.55 \times 10^{-7}$ M |
| Product of Example 56 | $3.4 \times 10^{-7}$ M |
| Product of Example 57 | $2.24 \times 10^{-7}$ M |
| Product of Example 64 | $1.4 \times 10^{-8}$ M |
| Product of Example 65 | $8.1 \times 10^{-9}$ M |
| Product of Example 66 | $4.2 \times 10^{-8}$ M |
| Product of Example 70B | $8.9 \times 10^{-8}$ M |

We claim:

1. A 1,4-dihydropyridine derivative of the formula:

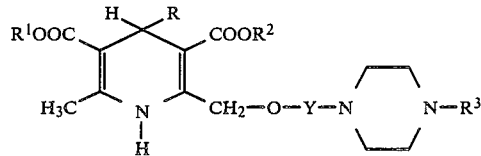

, or a pharmaceutically acceptable acid addition salt thereof, where

R is aryl or heteroaryl;

$R^1$ and $R^2$ are each independently $C_1$-$C_4$ alkyl or 2-methoxyethyl;

Y is $-(CH_2)_2-$, $-(CH_2)_3-$, $-CH_2CH(CH_3)-$ or $-CH_2C(CH_3)_2-$;

$R^3$ is hydrogen or is selected from the group consisting of:

(a)

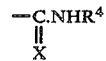

where $R^4$ is H, $C_1$-$C_4$ alkyl, $C_3$-$C_6$ cycloalkyl, $-COO(C_1$-$C_4$ alkyl), $-CH_2COO(C_1$-$C_4$ alkyl), aryl, $-SO_2$ aryl, or heteroaryl, and X is O or S;

(b)

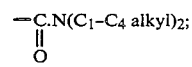

(c)

where $R^5$ is 1-pyrrolidinyl, $-NH_2$, $-NH(C_1$-$C_4$ alkyl), $-N(C_1$-$C_4$ alkyl)$_2$, or $-NH(CH_2)_2N(C_1$-$C_4$ alkyl)$_2$;

(d)

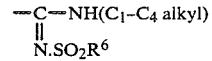

where $R^6$ is $C_1$-$C_4$ alkyl or aryl;

(e)

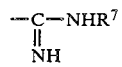

where $R^7$ is $-CONH(C_1$-$C_4$ alkyl) or $-COO(C_1$-$C_4$ alkyl);

(f)

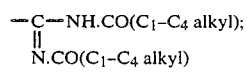

(g)

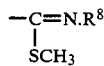

where $R^8$ is —CN, —SO$_2$(C$_1$–C$_4$ alkyl) or —SO$_2$ aryl;

(h) —CH$_2$CO.R$^9$ where R$^9$ is —NH$_2$, —NH(C$_1$–C$_4$ alkyl), —NH.aryl or C$_1$–C$_4$ alkoxy;

(i) —SO$_2$.R$^{10}$ where R$^{10}$ is —NH$_2$, —N(C$_1$–C$_4$ alkyl)$_2$ or C$_1$–C$_4$ alkyl; and (j) —CO.R$^{11}$ where R$^{11}$ is H, halomethyl, —COO(C$_1$–C$_4$ alkyl), —CH$_2$O(C$_1$–C$_4$ alkyl), —CH$_2$CO(C$_1$–C$_4$ alkyl), C$_1$–C$_4$ alkyl, C$_1$–C$_4$ alkoxy, aryl, heteroaryl, morpholino or 5-oxo-pyrrolidin-2-yl;

wherein the aryl is phenyl; phenyl substituted by one or two substituents selected from the group consisting of nitro, halo, C$_1$–C$_4$ alkyl, C$_1$–C$_4$ alkoxy, hydroxy, trifluoromethyl, (C$_1$–C$_4$ alkoxy)carbonyl and cyano; 1-naphthyl; or 2-naphthyl; and wherein the heteroaryl is benzofuranyl; benzothienyl; pyridyl; pyridyl substituted by methyl or cyano; quinolyl; benzoxazolyl; benzthiazolyl; furyl; pyrimidinyl; thiazolyl; 2,1,3-benz-oxadiazol-4-yl; 2,1,3-benzthiadiazol-4-yl; thienyl; or thienyl substituted by halo or C$_1$–C$_4$ alkyl.

2. A compound according to claim 1 wherein R$^1$ is CH$_3$, R$^2$ is C$_2$H$_5$ and R$^3$ is —CONH(C$_1$–C$_4$ alkyl).

3. A compound according to claim 2 wherein Y is —(CH$_2$)$_2$—.

4. A compound according to claim 1 wherein Y is —(CH$_2$)$_2$—.

5. A compound according to claim 1 wherein R is aryl.

6. A compound according to claim 5 wherein R$^1$ is CH$_2$, R$^2$ is C$_2$H$_5$ and R$^3$ is —CONH(C$_1$–C$_4$ alkyl).

7. A compound according to claim 6 wherein Y is —(CH$_2$)$_2$—.

8. A compound according to claim 5 wherein Y is —(CH$_2$)$_2$—.

9. A compound according to claim 5 wherein R is 2-chlorophenyl, 2-trifluoromethylphenyl, 2,3-dichlorophenyl, 3,5-dichlorophenyl, 2,6-dichlorophenyl, 1-naphthyl, 3-chlorophenyl or 2-fluorophenyl.

10. A compound according to claim 9 wherein R$^1$ is CH$_3$, R$^2$ is C$_2$H$_5$ and R$^3$ is —CONH(C$_1$–C$_4$ alkyl).

11. A compound according to claim 10 wherein Y is —(CH$_2$)$_2$—.

12. A compound according to claim 9 wherein Y is —(CH$_2$)$_2$—.

13. A compound according to claim 5 wherein R is 2,3-dichlorophenyl, R$^1$ is CH$_3$, R$^2$ is C$_2$H$_5$, Y is —(CH$_2$)$_2$— and R$^3$ is —CONH$_2$ or —CONHCH$_3$.

14. A compound according to claim 1 wherein R is heteroaryl.

15. A compound according to claim 14 wherein R$^1$ is CH$_3$, R$^2$ is C$_2$H$_5$ and R$^3$ is —CONH(C$_1$–C$_4$ alkyl).

16. A compound according to claim 15 wherein Y is —(CH$_2$)$_2$—.

17. A compound according to claim 14 wherein Y is —(CH$_2$)$_2$—.

18. A pharmaceutical composition comprising a heart condition treating or antihypertensive effective amount of a compound according to claim 1 and a pharmaceutically acceptable diluent or carrier.

19. A method of treating a heart condition, which comprises administering an effective amount of a compound according to claim 1.

20. A method of treating hypertension which comprises administering an effective amount of a compound according to claim 1.

* * * * *